(12) United States Patent
Lambert

(10) Patent No.: US 6,206,002 B1
(45) Date of Patent: Mar. 27, 2001

(54) DEVICE AND METHOD FOR RECOVERING ANAESTHETIC DURING THE USE OF INHALED ANAESTHETICS

(75) Inventor: Hans Lambert, Stockholm (SE)

(73) Assignee: Hudson RCI AB (SE)

( * ) Notice: Subject to any disclaimer, the term of this patent is extended or adjusted under 35 U.S.C. 154(b) by 0 days.

(21) Appl. No.: 09/313,579

(22) Filed: May 13, 1999

Related U.S. Application Data

(63) Continuation of application No. PCT/SE97/01861, filed on Nov. 6, 1997.

(51) Int. Cl.$^7$ ................................................. A61M 16/00
(52) U.S. Cl. ........................ 128/205.12; 128/205.27; 128/205.28; 128/205.29; 128/203.13
(58) Field of Search .................. 128/205.12, 205.27, 128/205.28, 205.29, 203.13

(56) References Cited

U.S. PATENT DOCUMENTS 4,905,685 * 3/1990 Olsson et al. .................. 128/203.12
5,471,979 * 12/1995 Psaros et al. .................. 128/205.28

FOREIGN PATENT DOCUMENTS 0496336  7/1992 (EP) .
8807876  10/1998 (WO) .

* cited by examiner

*Primary Examiner*—John G. Weiss
*Assistant Examiner*—Mital Patel
(74) *Attorney, Agent, or Firm*—Knobbe, Martens, Olson & Bear, LLP

(57) ABSTRACT

The invention relates to a device and method for recovering anaesthetic during the use of inhaled anaesthetics. An anaesthetic reflector (5) is used which absorbs anaesthetic medium from the gas exhaled by the patient and desorbs anaesthetic medium to the gas inhaled by the patient. According to the invention a moisture-heat exchanger (12) is arranged in the system which, in an equivalent manner, recovers water vapor from the gas exhaled to the gas inhaled. The moisture-heat exchanger (12) is preferably located between the anaesthetic reflector (5) and the patient (1). The device and the method according to the invention enable the gas inhaled to be moistened to prevent dehydration, as well as increasing the efficiency of the reflector (5).

9 Claims, 3 Drawing Sheets

DEVICE AND METHOD FOR RECOVERING ANAESTHETIC DURING THE USE OF INHALED ANAESTHETICS

CROSS-REFERENCE TO RELATED APPLICATIONS

This application is a continuation of PCT/SE97/01861, filed Nov. 6, 1997.

BACKGROUND OF THE INVENTION

The present invention relates a device and method for recovering anaesthetic during the use of inhaled anesthetics.

Such devices and methods are disclosed through SE-B 459 155 and SE-B-515 217, for instance. The purpose of such a device is to reduce the consumption of anaesthetic preparations when treating a patient, since preparations such as Fluothane-(2-bromine-2-chlorine-1,1,1-trifluorethane) are often relatively expensive. According to older, conventional technology the anaesthetic preparation is conducted away to the surroundings together with the air exhaled and is therefore lost, as well as contaminating the surroundings.

However, these devices are unable to compensate the loss of moisture upon exhalation. It would also be desirable to be able to improve the reflection efficiency, i.e. the proportion of exhaled anaesthetic which is absorbed and returned to the gas inhaled.

Against this background, the object of the present invention is to alleviate this deficiency in the known devices and methods, and to increase the reflection efficiency.

SUMMARY OF THE INVENTION

The present invention relates to a device comprising an anaesthetic reflector used for absorbing anaesthetic medium from the gas exhaled by the patient and desorbs anaesthetic medium to the gas inhaled by the patient. According to the invention a moisture-heat exchanger is arranged in the system, which in an equivalent manner recovers water vapor from the gas exhaled by the patient to the gas inhaled by the patient. The moisture-heat exchanger is preferably located between the anaesthetic reflector and the patient. The device and the method according to the invention enable the gas inhaled to be moistened to prevent dehydration, as well as increasing the efficiency of the reflector.

Thanks to the second unit with the ability to absorb and desorb water vapour, i.e. a moisture-heat exchanger, which is arranged in series with the first unit, i.e. the anaesthetic reflector, both anaesthetic and water vapour in the gas exhaled will be recovered since each component is absorbed in a separate unit. During inhaling, the anaesthetic preparation and water vapour recovered are released and desorbed out in the gases breathed, which will thus re-use a part of the anaesthetic preparation, as well as having part of its moisture content restored. The use of this device and this method thus enables a lower consumption of anaesthetic preparation than has been possible with known technology, as well as eliminating the need for any special supply of water vapour in order to avoid the risk of dehydration.

In a particularly preferred embodiment of the invention the second unit is situated between the patient and the first unit.

This has been found to have the surprising effect of greatly increasing the proportion of anaesthetic preparation recovered. It has been ascertained that the reflection efficiency is considerably increased with such an arrangement in comparison with other alternatives and even in comparison with a device without any moisture-heat exchanger at all. The optimal efficiency obtained with this preferred embodiment is probably a result of the reduced moisture content in the gas exhaled before it enters the anaesthetic reflector, increasing the ability of the after to absorb and desorb anaesthetic. A greater proportion of this will therefore be returned to the patient in the gas inhaled.

In another preferred embodiment, preferably a variation of that described above, both the units, i.e. the anaesthetic reflector and the moisture-heat exchanger, are located in a common housing. This simplifies the construction, making it more compact and easily managed. It also ensures that the two units are compatible from the point of view of size.

The supply means for the anaesthetic preparation is preferably arranged in the tube between the patient and the air-heat exchanger, which offers maximum utilization of the anaesthetic preparation as well as more reliable control of dosages. In this case the means suitably comprises an vaporizer arranged in the patient tube. The advantages of such an arrangement are further described in patent application SEB459 155 mentioned above.

The above and other advantageous embodiments of the device according to the invention are defined in the sub-claims to the main method claim.

Equivalent advantageous embodiments of the method according to the invention are defined in the sub-claims to the main method claim.

BRIEF DESCRIPTION OF THE DRAWINGS

The invention is described in more detail in the following description of preferred embodiments with reference to the accompanying drawings, in which.

DETAILED DESCRIPTION OF THE INVENTION

Figure 1:
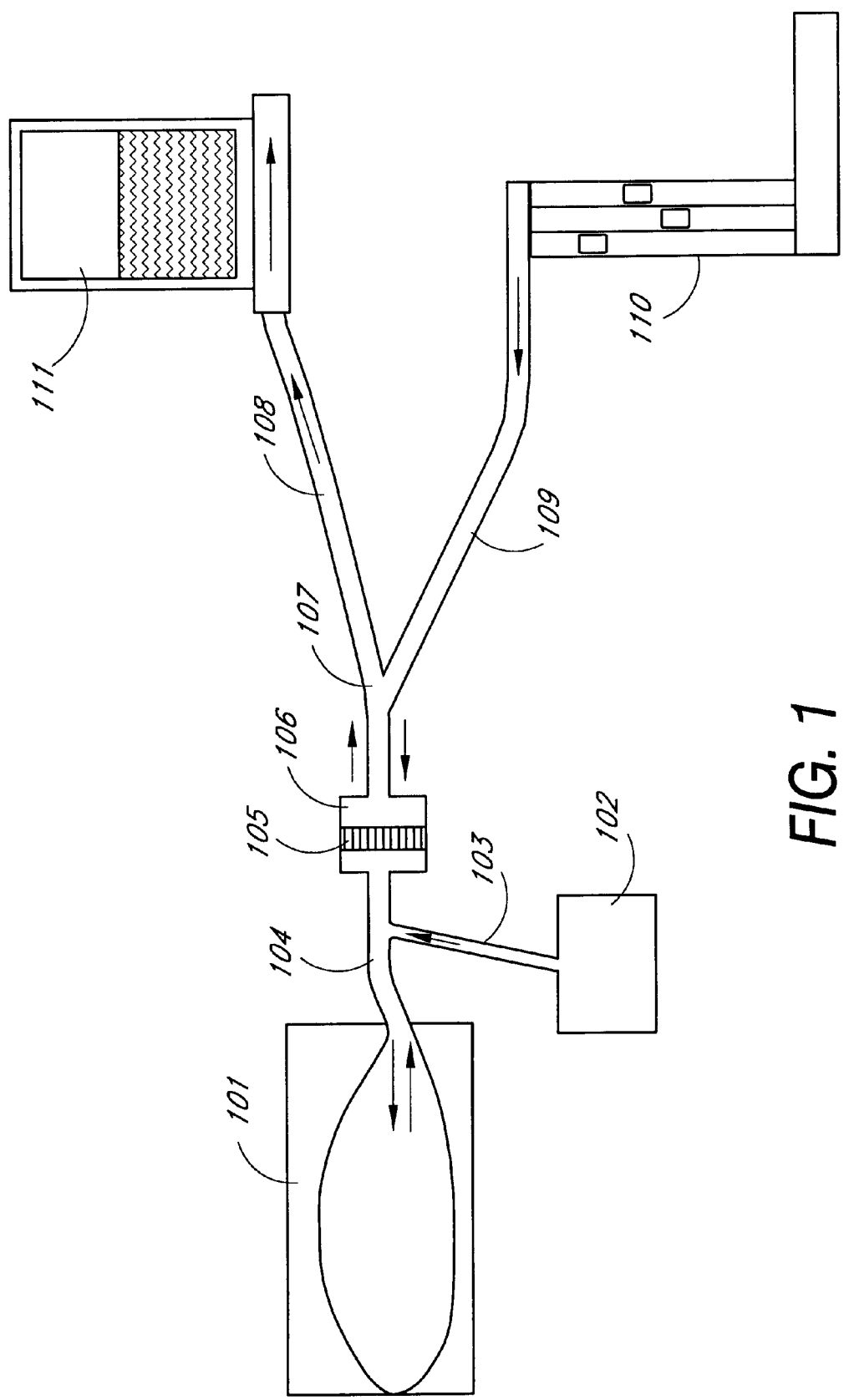
FIG. 1 illustrates schematically a reflector according to known technology.

In FIG. 1, which illustrates the principle for recovering anaesthetic according to known technology, 101 denotes a patient being treated with anaesthetic or an apparatus simulating the respiratory organs of a patient. The patient 101 is connected via the patient tube 104 to an anaesthetic reflector 105 arranged in a housing 106. A supply tube 103 for anaesthetic, connected to a supply 102 of anaesthetic, opens into the patient tube 104. The side of the reflector 105 facing away from the patient is connected via a Y-connection 107 to an outlet tube 108 for exhaled gas and an inlet tube 109 for inhaled gas, these being connected to a gas pump 111 and a gas supply device 110, respectively.

The reflector 105 consists of a material having the ability to absorb or desorb anaesthetic, e.g. woven active carbon. Measurements indicate that such a device is able to return 70% of the anaesthetic exhaled.

Figure 2:
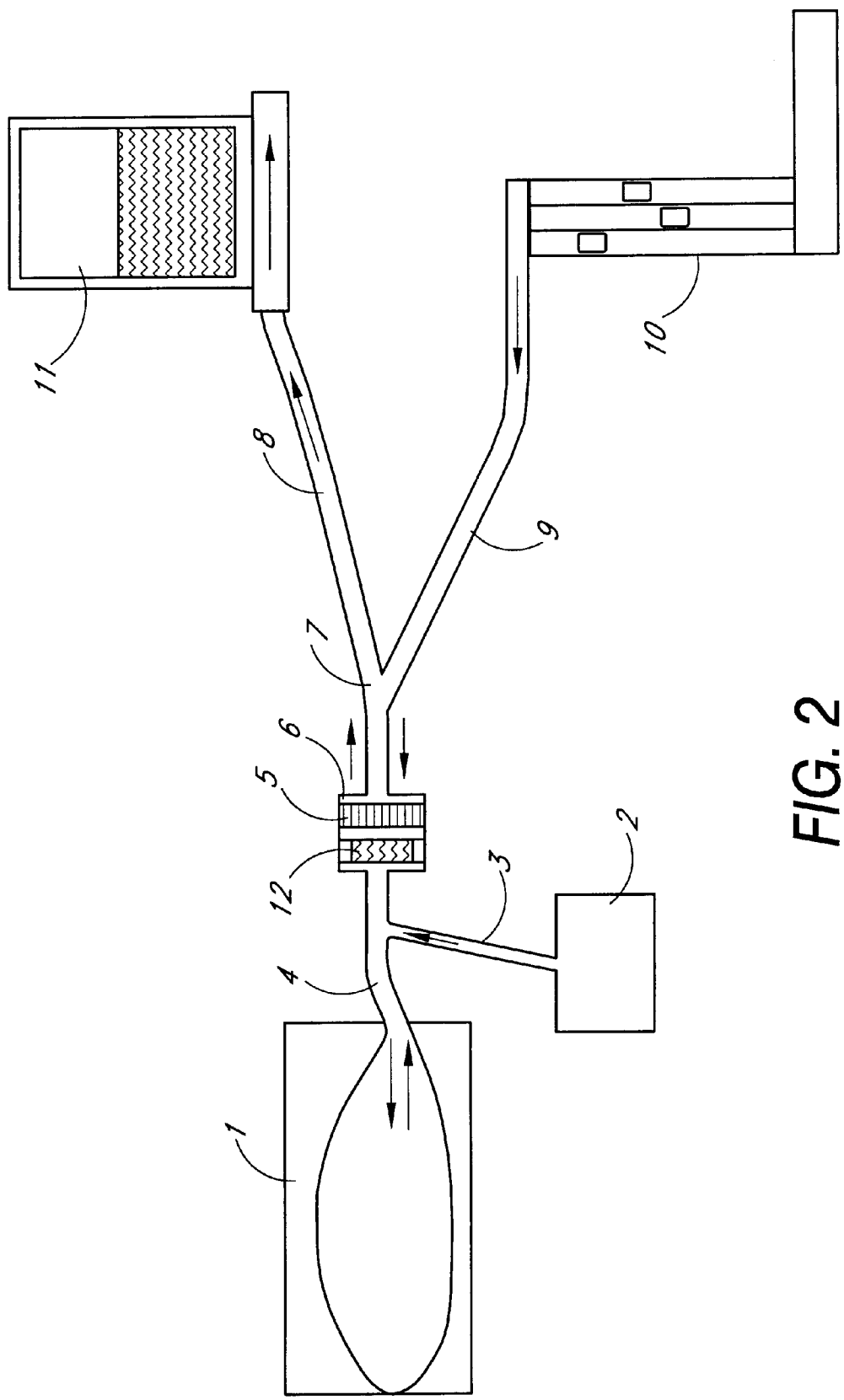
FIG. 2 illustrates schematically a preferred embodiment of the present invention.

The device according to the invention illustrated in an embodiment shown in FIG. 2 is constructed in an equivalent manner to that shown in Figure Accordingly, the device shown in FIG. 2 illustrates a patient 1 connected via patient tube 4 to an anaesthetic reflector 5 arranged in housing 6. A supply tube 3 for anaesthetic, connected to a supply 2 of anaesthetic, opens into the patient tube 4. The side of the reflector 5 facing away from the patient is connected via a Y-connection 7 to an outlet tube 8 for exhaled gas and an inlet tube 9 for inhaled gas, these being connected to a gas pump 11 and a gas supply device 10, respectively. The device illustrated in FIG. 2 includes a moisture-heat exchanger 12 which absorbs and desorbs the moisture in the gases breathed is arranged in the housing 6 on the side of the anaesthetic reflector facing the patient. Thanks to this arrangement the proportion of anaesthetic recovered is increased to 80%. At the same time about 80% of the water vapour exhaled is also returned to the patient. As is clear from the FIG. 2 the reflector 5 has a larger cross-sectional area than the moisture-heat exchanger, which has proved to be advantageous.

In FIG. 2 both the moisture-heat exchanger 12 and the anaesthetic reflector 5 are shaped as a cylindrical plate with axial through-flow. However, it will be understood that the shape is of minor significance. One or both of these units may be annular in shape, for instance, with radial through-flow direction, in which case they may be arranged radially one outside the other.

Figure 3:
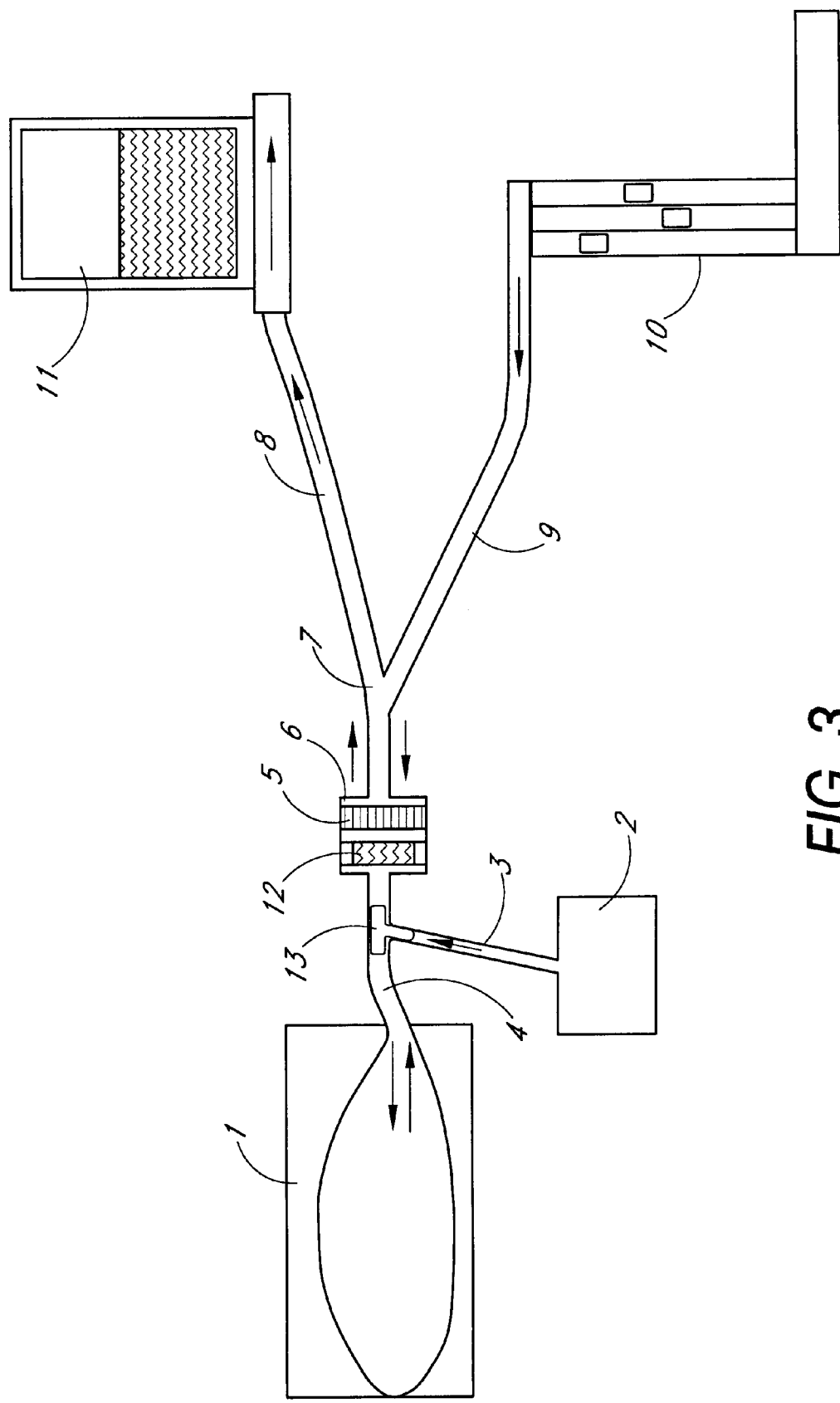
FIG. 3 illustrates schematically a second embodiment of the present invention.

The device according to FIG. 3 incorporates the same componenets designated by the same reference numerals shown in FIG. 2 but differs from that in FIG. 2 in that the anaesthetic preparation is supplied in liquid form through the tube 3 to the patient tube 4 and is only then vaporized in the patient tube via an anaesthetic vaporizer 13. This may be of a type described in more detail in the Swedish patent application No. 96010285 and offers certain advantages which are described in said patent application.

What is claimed is:

1. A device for recovering anaesthetic during the use of inhaled anesthetics, said device comprising a patient tube for connecting to a patient, and further comprising a first unit capable of absorbing and desorbing anaesthetic preparations, and a second unit arranged in series with the first unit between the first unit and the patient tube and being capable of absorbing and desorbing water vapor.

2. A device as claimed in claim 1, wherein said first unit and said second unit are arranged in a common housing.

3. A device as claimed in claim 1, wherein said first unit has a larger area transverse to the direction of flow of the gas than said second unit.

4. A device as claimed in claim 2, wherein said first unit has a larger area transverse to the direction of flow of the gas than said second unit.

5. A device as claimed in claim 4, including anaesthetic supply apparatus connected to the patient tube between said second unit and the patient.

6. A device as claimed in claim 5 wherein said anaesthetic supply apparatus comprises an anaesthetic vaporizer in said patient tube.

7. A method of recovering anaesthetic in an anesthesia circuit during the use of inhaled anesthetics, wherein the gases inhaled and exhaled by a patient are directed through a first unit for absorption of anaesthetic in the gas exhaled and desorption of anaesthetic to the gas inhaled, said method comprising providing a second unit in series with said first unit along said anaesthesia circuit capable of absorbing water vapor in the gases exhaled and desorbing water vapor in the gases inhaled, and supplying anaesthetic in the gas to be inhaled in a patient tube along the anesthesia circuit between said units and the patient.

8. A method as claimed in claim 7, wherein water vapor in the gases exhaled is absorbed before anaesthetic in the gas exhaled is absorbed, and anaesthetic is desorbed to the gases inhaled before water vapor is desorbed to the gases inhaled.

9. A method as claimed in claim 8 including supplying said anaesthetic in liquid form devaporized in said patient tube.

\* \* \* \* \*